United States Patent
Jeong et al.

(10) Patent No.: US 12,084,413 B2
(45) Date of Patent: Sep. 10, 2024

(54) CONTINUOUS PRODUCTION METHOD OF DIESTER-BASED MATERIAL

(71) Applicant: LG CHEM, LTD., Seoul (KR)

(72) Inventors: Jae Hun Jeong, Daejeon (KR); Sung Kyu Lee, Daejeon (KR); Yeon Uk Choo, Daejeon (KR); Hyun Kyu Kim, Daejeon (KR); Seok Goo Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 542 days.

(21) Appl. No.: 17/603,208

(22) PCT Filed: Jul. 2, 2020

(86) PCT No.: PCT/KR2020/008660
§ 371 (c)(1),
(2) Date: Oct. 12, 2021

(87) PCT Pub. No.: WO2021/002700
PCT Pub. Date: Jan. 7, 2021

(65) Prior Publication Data
US 2022/0185761 A1 Jun. 16, 2022

(30) Foreign Application Priority Data

Jul. 4, 2019 (KR) .................. 10-2019-0080460

(51) Int. Cl.
*C07C 67/08* (2006.01)
*B01J 19/00* (2006.01)
(Continued)

(52) U.S. Cl.
CPC .......... *C07C 67/08* (2013.01); *B01J 19/0066* (2013.01); *C07C 67/52* (2013.01); *C07C 69/75* (2013.01);
(Continued)

(58) Field of Classification Search
CPC ......... C07C 67/08; C07C 69/76; C07C 69/80; C07C 69/82; C07C 69/75; B01J 19/0066; B01J 2219/00033
See application file for complete search history.

(56) References Cited

U.S. PATENT DOCUMENTS 3,476,796 A * 11/1969 Adachi .................. C07C 67/08
560/99
2008/0163543 A1 7/2008 Abhari et al.
(Continued)

FOREIGN PATENT DOCUMENTS

CN 102256922 A 11/2011
CN 102256923 A 11/2011
(Continued)

*Primary Examiner* — Yate' K Cutliff
(74) *Attorney, Agent, or Firm* — Bryan Cave Leighton Paisner LLP (57) ABSTRACT

The present disclosure relates to a continuous production method of a diester-based material in a continuous production process comprising a reaction part in which a total of N reaction units from a first reaction unit to an N-th reaction unit are connected in series. The method comprising the step of feeding dicarboxylic acid and a primary alcohol, wherein the feed of the primary alcohol is divided into front-end feed of being fed into a first reaction unit and rear-end feed of being fed into one or more reaction units selected among from a second reaction unit to an N-th reaction unit, wherein the amount of the rear-end feed is 5 to 80 wt % based on the total feed amount of the primary alcohol into a reaction part, and the N is an integer of 3 to 6. According to the present invention, it is possible to ensure the ease of process operation through reducing the amount of reflux compared to a typical batch process and reducing the volume of steam for heating a reactor, and to ensure the economic feasibility of a product through saving energy.

10 Claims, 3 Drawing Sheets

(51) Int. Cl.
  *C07C 67/52* (2006.01)
  *C07C 69/75* (2006.01)
  *C07C 69/80* (2006.01)
  *C07C 69/82* (2006.01)

(52) U.S. Cl.
  CPC .............. *C07C 69/80* (2013.01); *C07C 69/82* (2013.01); *B01J 2219/00033* (2013.01); *B01J 2219/0004* (2013.01)

(56) References Cited

U.S. PATENT DOCUMENTS

| | | | |
|---|---|---|---|
| 2011/0251420 A1* | 10/2011 | Disteldorf | C07C 67/08 560/99 |
| 2011/0301377 A1 | 12/2011 | Peters | |
| 2013/0085288 A1 | 4/2013 | Snead et al. | |
| 2015/0141691 A1 | 5/2015 | Disteldorf et al. | |
| 2015/0299613 A1 | 10/2015 | Snead et al. | |
| 2019/0263745 A1 | 8/2019 | Lee et al. | |
| 2021/0040026 A1 | 2/2021 | Lee et al. | |

FOREIGN PATENT DOCUMENTS

| | | | | |
|---|---|---|---|---|
| CN | 102295564 A | 12/2011 | | |
| CN | 102503831 A | 6/2012 | | |
| CN | 106674010 A | 5/2017 | | |
| CN | 107857896 A | 3/2018 | | |
| JP | S52-19601 A | 2/1977 | | |
| JP | H11-049726 A | 2/1999 | | |
| JP | 11-130724 A | 5/1999 | | |
| JP | 2012-512229 A | 5/2012 | | |
| KR | 10-0338042 B1 | 12/2002 | | |
| KR | 10-2011-0101205 A | 9/2011 | | |
| KR | 10-2011-0101206 A | 9/2011 | | |
| KR | 10-2013-0042742 A | 4/2013 | | |
| KR | 10-1663586 B1 | 10/2016 | | |
| KR | 10-2019-0027622 A | 3/2019 | | |
| KR | 10-2019-0027623 A | 3/2019 | | |
| KR | 10-2019-0066560 A | 6/2019 | | |
| NL | 2021197 | * | 6/2018 | ............ C07C 67/08 |
| WO | 2010-076192 A1 | 7/2010 | | |
| WO | 2010-076194 A1 | 7/2010 | | |

* cited by examiner

CONTINUOUS PRODUCTION METHOD OF DIESTER-BASED MATERIAL

CROSS-REFERENCE TO RELATED APPLICATIONS

This application is a National Phase entry pursuant to 35 U.S.C. § 371 of International Application No. PCT/KR2020/008660, filed on Jul. 2, 2020, and claims the benefit of and priority to Korean Patent Application No. 10-2019-0080460, filed on Jul. 4, 2019, in the Korean Intellectual Property Office, all of which are hereby incorporated by reference in their entirety for all purposes as if fully set forth herein.

TECHNICAL FIELD

Technical Field

The present invention relates to a continuous production method of a diester-based material, in which a portion of a feed raw material is divided to control the content and position of the feed raw material.

Background Art

Phthalate-based plasticizers had occupied 92% of the world's plasticizer market by the 20th century (Mustafizur Rahman and Christopher S. Brazel "The plasticizer market: an assessment of traditional plasticizers and research trends to meet new challenges" Progress in Polymer Science 2004, 29, 1223-1248), and are additives used to improve the processability of polyvinyl chloride (hereinafter, referred to as PVC) by imparting flexibility, durability, cold resistance, and the like and lowering viscosity during melting. Phthalate-based plasticizers are introduced into PVC in various contents and used not only for hard products such as rigid pipes, but also for soft products such as food packaging materials, blood bags, and flooring materials since the phthalate-based plasticizers are soft and stretchable. Thus, the phthalate-based plasticizers are more closely related to real life than any other materials and are widely used for materials which come into direct contact with a human body.

However, despite the compatibility with PVC and excellent softness imparting properties of phthalate-based plasticizers, there has been controversy over the harmful nature of the phthalate-based plasticizers in that when a PVC product containing a phthalate-based plasticizer is used in real life, the phthalate-based plasticizer can be leaked little by little out of the product and act as a suspected endocrine disruptor (environmental hormone) and a carcinogen to the level of a heavy metal (N R Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2008, 42, 7522-7527). Particularly, since a report was published in the 1960s in the United States that diethylhexyl phthalate (di-(2-ethylhexyl) phthalate, DEHP), the most used phthalate plasticizer, leaked out of PVC products, global environmental regulations have started to be implemented in addition to various studies on the harmful nature of the phthalate-based plasticizer on human bodies, boosted by increasing interest in environmental hormones in the 1990s.

Thus, in order to respond to environmental hormonal problems and environmental regulations due to the leakage of a phthalate-based plasticizer, di(2-ethylhexyl) phthalate in particular, many researchers have been conducting research in order to develop a new non-phthalate-based alternative plasticizer without phthalic anhydride used in the manufacturing of di(2-ethylhexyl) phthalate, and to develop a phthalate-based plasticizer which can replace di(2-ethylhexyl) phthalate and be used for industrial purposes since the leakage of the plasticizer is suppressed even though it is based on phthalate, as well as to develop a leakage suppression technology which suppresses the leakage of phthalate-based plasticizers, thereby significantly reducing risks to human bodies and which meets environmental standards.

As such, as diester-based plasticizers, the development of materials which are free from environmental problems and which can replace a di(2-ethylhexyl) phthalate having existing environmental problems is actively underway. In addition, research on developing a diester-based plasticizer with excellent physical properties as well as research on equipment for manufacturing the plasticizer have been actively conducted, and there has been a demand for more efficient, more economical and simpler process designs in terms of process design.

Meanwhile, a batch process is being applied in most industrial sites as a process of producing the above diester-based plasticizer. As the batch process, an invention related to a gas-liquid separation system for the reflux of non-reactants and efficient removal of sub-reactants in a reactor (Korean Patent Laid-Open Publication No. 10-2019-0027622) and an invention related to a system integrating facilities of a primary direct esterification reaction and a second trans-esterification reaction in order to simplify facilities of a batch process (Korean Patent Laid-Open Publication No. 10-2019- 0027623) have been introduced. However, as a batch process, such inventions have limitations in that there is a limit to the improvement in the amount of reflux or the volume of steam, the productivity is very low, and there is a limit to the technology which can be applied for improvement.

In addition, as a continuous process, an invention related to a process configuring a reaction part by connecting two or more reactors in series (Korean Patent Publication No. 10-1663586) has also been introduced. However, the invention relates to the control of a reaction temperature of a reactor for achieving a target conversion, and there is a limit to the improvement of a process and energy saving.

PRIOR ART DOCUMENT

Patent Document (Patent Document 1) Korean Patent Laid-Open Publication No. 10-2019-0027622

(Patent Document 2) Korean Patent Laid-Open Publication No. 10-2019-0027623

(Patent Document 3) Korean Patent Laid-Open Publication No. 10-1663586

DISCLOSURE OF THE INVENTION

Technical Problem

An aspect of the present invention provides a production method of a diester-based material, in which a feed raw material is divided in a process of continuously producing the diester-based material and the amount and position of the raw material dividedly fed are controlled to reduce the volume of steam supplied to a reactor and reduce the amount of reflux generated due to vaporization, thereby ensuring cost competitiveness of a final product.

Technical Solution

According to an aspect of the present invention, there is provided a continuous production method of a diester-based material in a continuous production process of a diester-based material, the process comprising a reaction part in which a total of N reaction units from a first reaction unit to an N-th reaction unit are connected in series, wherein the method comprises feeding dicarboxylic acid and a primary alcohol, wherein the feed of the primary alcohol is divided into front-end feed of being fed into a first reaction unit and rear-end feed of being fed into one or more reaction units selected among from a second reaction unit to an N-th reaction unit, the amount of the rear-end feed is 5 to 80 wt % based on the total feed amount of the primary alcohol into a reaction part, and the N is an integer of 3 to 6.

Advantageous Effects

In the present invention, while a primary alcohol among raw materials for producing a diester-based material is divided into two or more, the amount of the primary alcohol dividedly fed and the position of the primary alcohol dividedly fed are controlled, so that the volume of steam required for a reactor and the amount of reflux which is the amount of unreacted materials vaporized in the reactor returning to the reactor can be significantly reduced.

MODE FOR CARRYING OUT THE INVENTION

Hereinafter, the present invention will be described in more detail to facilitate understanding of the present invention.

It will be understood that words or terms used in the description and claims of the present invention shall not be construed as being limited to having the meaning defined in commonly used dictionaries. It will be further understood that the words or terms should be interpreted as having meanings that are consistent with their meanings in the context of the relevant art and the technical idea of the invention, based on the principle that an inventor can properly define the meaning of the words or terms to best explain the invention.

According to an embodiment of the present invention, a continuous production method of a diester-based material is performed in a continuous production process including a reaction part in which a total of N reaction units from a first reaction unit to an N-th reaction unit are connected in series.

Also, the production method includes feeding one or more dicarboxylic acids selected from the group consisting of terephthalic acid, phthalic acid, isophthalic acid, and cyclohexane dicarboxylic acid and a primary alcohol having 3 to 10 carbon atoms.

In addition, the feed of the primary alcohol is divided into front-end feed of being fed into a first reaction unit and rear-end feed of being fed into one or more reaction units selected among from a second reaction unit to an N-th reaction unit, wherein the amount of the rear-end feed is 5 to 80 wt % based on the total feed amount of the primary alcohol, and the N is an integer of 3 to 6.

Hereinafter, a reaction applied to the production method according to an embodiment of the present invention will be described.

The production method of the present invention is a method for producing a diester-based material, and can be a method to which a direct esterification reaction in which dicarboxylic acid and a primary alcohol react can be applied.

As the dicarboxylic acid, one or more selected from the group consisting of terephthalic acid, phthalic acid, isophthalic acid, and cyclohexane dicarboxylic acid are applied, and as the primary alcohol, one having 3 to 10 carbon atoms is applied. As long as the carbon number is satisfied, the primary alcohol can have a linear or branched alkyl group and can be a mixture in which linear and branched types are mixed, wherein the branched type can be a mixture including one or more structural isomers.

Representative diester-based materials prepared through the above are terephthalate, isophthalate, phthalate, cyclohexane 1,2-diester, cyclohexane 1,3-diester, or cyclohexane coupled with an alkyl group derived from the primary alcohol and these materials are plasticizer series which can replace di(2-ethyl hexyl) phthalate plasticizer causing environmental problems. However, when phthalic acid is applied as dicarboxylic acid, 2-ethylhexanol can be excluded from being applied as the primary alcohol. The continuous production method of a diester-based material of the present invention can be applicable if the basic conditions of the materials are dicarboxylic acid and a primary alcohol having 3 to 10 carbon atoms.

The production method according to an embodiment of the present invention is a direct esterification reaction, and general conditions applied in the art can be applied as to reaction temperature and duration, and the type and content of a catalyst under which the direct esterification reaction can be performed.

Raw materials used in the production of the diester-based material are dicarboxylic acid and a primary alcohol as described above, and the dicarboxylic acid and the primary alcohol react in a molar ratio of 1:2 in theory. Accordingly, the feed amount of the dicarboxylic acid fed as a raw material and the total feed amount of the primary alcohol fed into a reaction part can be 1:2 to 1:5 in a molar ratio.

The above molar ratio is in a range which satisfies the minimum amount required for the reaction, and can be to prevent energy loss due to unnecessary reflux caused by the feed of an excessive amount of alcohol and can be determined in consideration of the excess amount of alcohol required in terms of achieving the conversion rate of the reaction and controlling the minimum residence time. The molar ratio can preferably be 1:2 to 1:4, and in order to optimally reflect the above, a molar ratio of 1:2.5 to 1:4, or 1:2.5 to 1:3.5 can be applied.

Hereinafter, a process to which the production method is applied will be described with reference to the accompanying drawings.

According to an embodiment of the present invention, the continuous production method of a diester-based material is performed in a continuous production process including a reaction part in which a total of N reaction units from a first reaction unit to an N-th reaction unit are connected in series.

The reaction unit is configured by connecting a total of N reaction units in series, and can be designed in consideration of controlling the conversion rate control of the reaction and the residence time in each reaction unit, and in consideration of the composition of a product to be produced. The number of reaction units can be 3 to 6, preferably 3 to 5, and 3 or 4 reaction units can be optimally applied.

Figure 1:
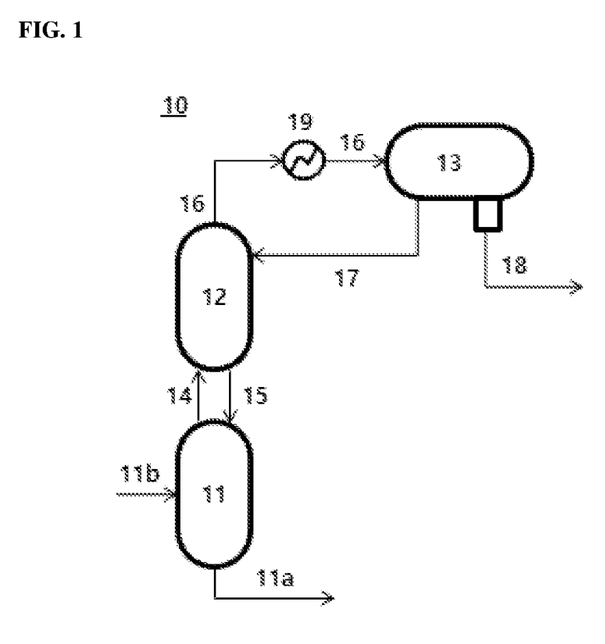
FIG. 1 is a process diagram showing one reaction unit applied to the present invention.

FIG. 1 illustrates one reaction unit 10, and the reaction unit 10 can include a reactor 11 in which an esterification reaction of dicarboxylic acid and a primary alcohol is performed, a column 12 in which the primary alcohol vaporized during the esterification reaction and water are introduced from the reactor to cause gas-liquid separation and then a liquid phase is fed into a lower reactor and a gas phase is discharged from an upper portion of the column, a condenser 19 which liquefies the gas phase discharged from the upper portion of the column to convert the liquefied gas phase into a liquid phase mixture, and a layer separator 13 in which the layer separation of the liquid phase mixture into an organic layer and an aqueous layer is performed, and then the separated organic layer is fed into an upper end of the column.

More specifically, dicarboxylic acid and a primary alcohol are fed through a raw material feed line 11b to be subjected to an esterification reaction. The raw material feed line 11b can have a pre-mixer (not shown) further installed at a front end to inject raw materials into the pre-mixer, thereby supplying the raw materials to a reactor, or can supply raw materials by performing line mixing with one raw material input line 11b. Alternatively, raw materials can be supplied through different feed lines for each raw material. The feed method of raw materials is not particularly limited as long as it is a method capable of supplying the raw materials into a reactor.

As the reaction is performed, the primary alcohol participates in the reaction, but in the reactor 11, there can inevitably be an amount which does not participate in the reaction but vaporized as the esterification reaction occurs above the boiling point of the primary alcohol. At the same time, water other than a diester-based material is generated as a reaction product, and the water is vaporized together with the primary alcohol and moved to the column 12 above the reactor 11, and at this time, can be moved through a gas phase discharge line 14. Meanwhile, when the reaction is performed above a predetermined conversion rate in the reactor 11, the diester-based material generated by the reaction can be transferred to the next reaction unit through a product line 11a.

In the column 12, a gas-phase primary alcohol introduced from the reactor 11 can be liquefied due to a liquid-phase primary alcohol fed into an upper end of the column 12 from a layer separator 13 through an organic layer line 17, and most of the gas-phase primary alcohol is selectively liquefied, and thus, the liquid-phase primary alcohol is fed back into the reactor 11 through the liquid phase introduction line 15, which can participate in the reaction again.

Gas-phase water and a portion of non-liquefied primary alcohol can be introduced into the layer separator 13 through the column upper line 16 on the upper end of the column 12, and in the layer separator, the primary alcohol and the water can be separated into an organic layer and an aqueous layer, respectively. The separated organic layer can be discharged to the column 12 through the organic layer line 17, and the separated aqueous layer can be discharged to the outside of a system through an aqueous layer line 18, or generated water can be utilized through various routes.

Meanwhile, the layer separator 13 is a facility in which the liquid-phase primary alcohol and the water are separated, and in this regard, the gas-phase primary alcohol and the water need to be liquefied in the layer separator 13 or before being fed into the layer separator 13. Accordingly, in a reaction unit of the production method according to an embodiment of the present invention, a condenser 19 is installed in the middle of the column upper line 16 connecting the column 12 and the layer separator 13, and since the heat of the gas phase-primary alcohol and the water are removed through the condenser 19, the gas-phase primary alcohol and the water are liquefied before being fed into the layer separator 13.

Figure 2:
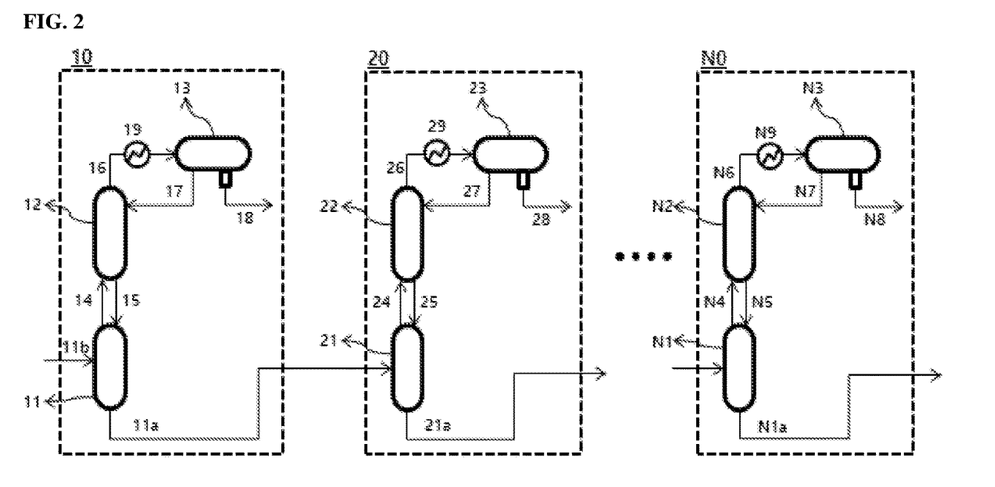
FIG. 2 is a process diagram showing a process of continuous production of a diester-based material according to an embodiment of the present invention.

FIG. 2 is a process diagram illustrating an entire reaction part to which the production method according to an embodiment of the present invention is applied, which illustrates a first reaction unit 10, a second reaction unit 20, and all the other reaction units up to a final N-th reaction unit N0.

The configuration of each of the reaction units 10, 20, and N0 illustrated in FIG. 2 can be a combination of facilities which perform the same function, and the movement of a reaction product of a front end reaction unit between each reaction unit can occur through product lines 11a, 21a, N1a from a front end reactor to a rear end reactor. The conversion rate and residence time of a reactor in each reaction unit, and the amount of reflux or the volume of steam in each reaction unit can be different from each other.

In the continuous production method of a diester-based material according to an embodiment of the present invention, the feed of the primary alcohol is divided into front-end feed of being fed into the first reaction unit and rear-end feed of being fed into one or more reaction units selected among from the second reaction unit to the N-th reaction unit, wherein the amount of the rear-end feed is 5 to 80 wt % based on the total feed amount of the primary alcohol in the reaction part.

As described above, in the production method of the present invention, it is common to inject an excess amount of the primary alcohol above an equivalent ratio for purposes such as keeping the concentration of a reactant high and compensating for a reactant lost due to the vaporization of the alcohol, which is the reactant, occurring since the reaction is performed at a temperature above the boiling point of the primary alcohol, in that the esterification reaction, which is an applied reaction, is an equilibrium reaction.

The feed of an excess amount of a primary alcohol can also be applied in a batch process. In this case, an optimal excess amount required for the entire process is calculated and fed into an initial reactor at once to proceed with a reaction. Even in a typical continuous process, it is common to calculate an optimal excess amount required for the entire process and mix raw materials through a pre-mixer to inject as a mixture at once, or have a separate line for each reactant and inject into a reactor at once.

However, in the case of feeding the excess amount of alcohol into the initial reactor at once, there is a limit to the conversion rate of the reaction which can proceed in the initial reactor. When the alcohol is fed above the limit, the amount of reflux unnecessarily increases, and the amount of steam required for heating the reactor increases due to the increase in the amount of raw materials, so that there is a problem of the deterioration in product cost competitiveness due to the increase in operating cost and the increase in energy cost of the entire process.

Accordingly, in the method for producing a diester-based material according to an embodiment of the present invention, by applying the divided feed of a primary alcohol to be fed into front-end feed of being fed into a first reaction unit and rear-end feed of being fed into a subsequent reaction unit, it is possible to significantly reduce the amount of reflux of alcohol and the volume of steam required for heating a reactor.

According to an embodiment of the present invention, the amount of the rear-end feed is 5 to 80 wt % based on the total feed amount of the primary alcohol in the reaction part as described above. When the content of the primary alcohol subjected to the rear-end feed is less than 5 wt %, the front-end feed amount fed into the first reaction unit is relatively increased, and thus, the reduction in the amount of reflux in the first reaction unit does not occur. When greater than 80 wt %, reactants are decreased in the first reaction unit, and thus, the conversion rate is not increased and passed to the second reaction unit, so that the load of the reaction of which the conversion rate is not increased is received by reaction units after the second reaction unit. Eventually, the amount of reflux after a reaction unit subjected to the rear-end feed can be greatly increased.

Accordingly, in order to reduce the amount of reflux and the volume of steam for heating the reactor, it is necessary to control the rear-end feed amount of the primary alcohol to be 5 to 80 wt %, preferably 10 to 70 wt %, more preferably 10 to 50 wt %, so that an optimal effect can be expected.

According to an embodiment of the present invention, the primary alcohol is subjected to front-end feed of being fed into the first reaction unit and the above-described rear-end feed amount is subjected to rear-end feed of being fed into one or more reaction units selected among from the second reaction unit to the N-th reaction unit. The rear-end feed can be fed into any one reaction unit selected among from the second reaction unit to the N-th reaction unit as one route, but can be preferably fed into the second reaction unit. In view of the conversion of the reaction, it can be desirable to inject the primary alcohol into a reaction unit close to the first reaction unit.

Alternatively, the rear-end feed can be achieved by feeding a portion into the second reaction unit and feeding the remaining portion into any one reaction unit selected among from the third reaction unit to the N-th reaction unit as using two routes, in which case, preferably feeding into an (N-1)-th reaction unit or the N-th reaction unit. In terms of reducing the volume of steam and the amount of reflux, it is preferable that the remaining portion is fed into the N-th reaction unit, but in terms of the conversion rate, it can be advantageous that the remaining portion is fed into the (N-1)-th reaction unit.

Furthermore, as using three routes, a portion of the rear-end feed amount can be fed into each of the second reaction unit and the third reaction unit and the remaining portion can be fed into any one reaction unit selected among from a fourth reaction unit to the N-th reaction unit, and preferably, can be into the fourth reaction unit.

The number of routes used for the rear-end feed can be appropriately selected according to the number of total reaction units. The number of routes for the rear-end feed can be at most N-1, preferably N-2. However, when considering the process design and simplification of lines, it can be preferable that the total number of reaction units, and independently, the number of routes do not exceed 2 since the effect of reducing the amount of reflux and the volume of steam which can be obtained can be relatively less when compared to opening several routes.

In addition, the front-end feed of the primary alcohol is achieved by feeding the same into the first reaction unit. In this case, as illustrated in FIG. 1, the feed can be achieved through the raw material feed line 11b, and the raw material feed line 11b can be formed as a separate line through which the primary alcohol and the dicarboxylic acid flow. A mixer can be further included at the front-end of the reaction part in the production process, and the primary alcohol can be subjected to the front-end feed to the mixer. The application of the mixer can be to vary the contact point of a raw material mixture and a catalyst, and the effect of preventing a side reaction with the catalyst can be obtained through the pre-heating of the raw material mixture before the contact with the catalyst. Alternatively, the mixer can be a facility which allows a heat exchange system to be built more efficiently in establishing a heat exchange network.

Figure 3:
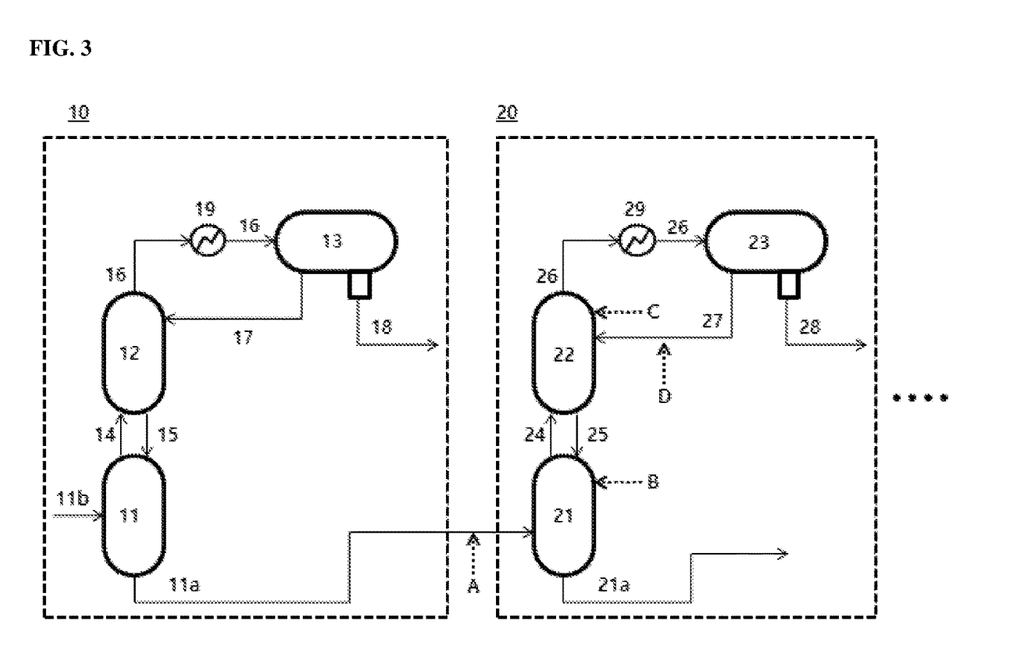
FIG. 3 is a process diagram indicating the position of a raw material dividedly fed in a process of continuous production of a diester-based material according to an embodiment of the present invention.

According to an embodiment of the present invention, in subjecting the primary alcohol to the rear-end feed, the position of the feed can be variously applied. FIG. 3 illustrates the position of a primary alcohol subjected to the rear-end feed. There can be the product line feed (A) of feeding into a line from the first reaction unit to the second reaction unit and from a reactor of one reaction unit to a reactor of another reaction unit, the reactor feed (B) of feeding directly into the reactor 21 (B), the column upper portion feed (C) of feeding into the upper portion of the column 22 of the second reaction unit, and the column upper line feed (D) of feeding into a line fed into the front end of the column 22. Among the three feed position, it can be preferable that the (C) feed is applied in terms of improving the efficiency of gas-liquid separation in a column.

Here, FIG. 3 exemplarily illustrates the case in which there is one route for the rear-end feed of a primary alcohol. As described above, there can be two or more routes. Even when there is one route, the rear-end feed into the third reaction unit, not the second reaction unit, can be applied. That is, when the primary alcohol is subjected to the rear-end feed, the feed position can be understood as the line feed (A) into a line introduced to a reactor of the N-th reaction unit subjected to the rear-end feed, the direct feed into a reactor (B), the column upper portion feed (C), and the line feed (D) into a line fed into the upper portion of a column.

EXAMPLES

Hereinafter, the present invention will be described in detail with reference to Examples. However, the following examples are merely illustrative of the present invention and are not intended to limit the scope of the present invention.

In the following Examples and Comparative Examples, a process system according to the continuous production method of a diester-based material according to the present invention, has been simulated by using CONTINUOUS MODELER in a commercial process simulation program ASPEN PLUS.

Experimental Example 1

In performing simulation using the above program, the simulation has been performed by the process illustrated in FIG. 2, wherein N was 4, dicarboxylic acid was terephthalic acid and a primary alcohol was 2-ethylhexanol as raw materials, and the molar ratio of the two raw materials was set to 1:2.5. While applying rear-end feed to a second reaction unit as one route, the feed position was set to be a column upper portion, and the amount of the rear-end feed was varied as shown in Table 1 below. The total steam volume of a reactor was measured in all four reaction units, and the total flow rate of the column upper portion was confirmed to measure the amount of reflux. In all Comparative Examples and Examples, the reactor steam volume and the total column upper portion flow rate were compared under the condition that the conversion rate reached 99.9%.

TABLE 1

| | Rear-end feed amount | Reactor steam volume | Whole column Upper flow rate |
|---|---|---|---|
| Comparative Example 1-1 | 0 | 100 | 100 |
| Example 1-1 | 10 | 91 | 90 |
| Example 1-2 | 20 | 86 | 83 |
| Example 1-3 | 50 | 87 | 83 |
| Example 1-4 | 70 | 98 | 95 |

* The volume of steam and the amount of reflux are relative % assuming that Comparative Example 1-1 is 100%.

Referring to Table 1 above, it can be confirmed that the volume of steam required for heating the reactor and the amount of reflux of the primary alcohol were greatly changed depending on the feed amount of the primary alcohol subjected to the rear-end feed. In the case of Comparative Example 1-1 to which divided feed was not applied, it can be confirmed that the volume of steam and the amount of reflux were considerably larger than those of Examples 1-1 to 1-4.

Experimental Example 2

In performing simulation using the above program, the simulation has been performed by the process illustrated in FIG. 2, wherein N was 4, dicarboxylic acid was terephthalic acid and a primary alcohol was 2-ethylhexanol as raw materials, and the molar ratio of the two raw materials was set to 1:3. While applying rear-end feed to a second reaction unit as one route, the feed position was set to be a column upper portion, and the amount of the rear-end feed was varied as shown in Table 2 below. The total steam volume of a reactor was measured in all four reaction units, and the total flow rate of the column upper portion was confirmed to measure the amount of reflux. In all Comparative Examples and Examples, the reactor steam volume and the total column upper portion flow rate were compared under the condition that the conversion rate reached 99.9%.

TABLE 2

| | Rear-end feed amount(wt %) | Reactor steam volume | Whole column Upper flow rate |
|---|---|---|---|
| Comparative Example 2-1 | 0 | 100 | 100 |
| Example 2-1 | 10 | 87 | 85 |
| Example 2-2 | 20 | 77 | 75 |
| Example 2-3 | 50 | 80 | 77 |
| Example 2-4 | 70 | 95 | 95 |

* The volume of steam and the amount of reflux are relative % assuming that Comparative Example 2-1 is 100%.

Referring to Table 2 above, it can be confirmed that the volume of steam required for heating the reactor and the amount of reflux of the primary alcohol were greatly changed depending on the content of the primary alcohol subjected to the rear-end feed. In the case of Comparative Example 2-1 to which divided feed was not applied, it can be confirmed that the volume of steam and the amount of reflux were considerably larger than those of Examples 2-1 to 2-4.

Experimental Example 3

In performing simulation using the above program, the simulation has been performed by the process illustrated in FIG. 2, wherein N was 4, dicarboxylic acid was terephthalic acid and a primary alcohol was 2-ethylhexanol as raw materials, and the molar ratio of the two raw materials was set to 1:4. While applying rear-end feed to a second reaction unit as one route, the feed position was set to be a column upper portion, and the amount of the rear-end feed was varied as shown in Table 3 below. The total steam volume of a reactor was measured in all four reaction units, and the total flow rate of the column upper portion was confirmed to measure the amount of reflux. In all Comparative Examples and Examples, the reactor steam volume and the total column upper portion flow rate were compared under the condition that the conversion rate reached 99.9%.

TABLE 3

| | Rear-end feed amount | Reactor steam volume | Whole column Upper flow rate |
|---|---|---|---|
| Comparative Example 3-1 | 0 | 100 | 100 |
| Example 3-1 | 10 | 59 | 57 |
| Example 3-2 | 20 | 52 | 50 |
| Example 3-3 | 50 | 40 | 38 |
| Example 3-4 | 70 | 53 | 51 |

* The volume of steam and the amount of reflux are relative % assuming that Comparative Example 3-1 is 100%.

Referring to Table 3 above, it can be confirmed that the volume of steam required for heating the reactor and the amount of reflux of the primary alcohol were greatly changed depending on the feed amount of the primary alcohol subjected to the rear-end feed. In the case of Comparative Example 3-1, it can be confirmed that the volume of steam and the amount of reflux were considerably larger than those of Examples 3-1 to 3-4.

Experimental Example 4

In performing simulation using the above program, the simulation has been performed by the process illustrated in FIG. 2, wherein N was 4, dicarboxylic acid was terephthalic acid and a primary alcohol was 2-ethylhexanol as raw materials, and the molar ratio of the two raw materials was set to 1:2.5. One or two routes were applied to rear-end feed as shown in Table 4 below, and the feed position was also varied as shown in Table 4. While varying the rear-end feed amount as shown in Table 4, the simulation was performed, and the total steam volume of a reactor was measured in all four reaction units, and the total flow rate of the column upper portion was confirmed to measure the amount of reflux. In all Comparative Examples and Examples, the reactor steam volume and the total column upper portion flow rate were compared under the condition that the conversion rate reached 99.9%.

TABLE 4

| | Rear-end feed amount | Reaction unit of rear-end feed | Position of rear-end feed | Reactor steam volume | Whole column Upper flow rate |
|---|---|---|---|---|---|
| Comparative Example 1-1 | 0 | — | — | 100 | 100 |
| Example 4-1 | 30 | 2 | Reactor feed line | 75 | 70 |
| Example 4-2 | 30 | 2 | Reactor feed line | 75 | 70 |
| Example 4-3 | 30 | 2 | Column upper portion | 74 | 69 |
| Example 4-4 | 30 | 2 and 3 | Column upper portion | 84 | 80 |
| Example 4-5 | 30 | 2 and 4 | Column upper portion | 90 | 85 |

* The volume of steam and the amount of reflux are relative % assuming that Comparative Example 1-1 is 100%.

Referring to Table 4 above, it can be confirmed that the volume of steam required for heating the reactor and the amount of reflux of the primary alcohol were greatly changed depending on the feed position of the primary alcohol subjected to the rear-end feed. In Examples 4-1 and 4-2 in which the primary alcohol is fed into the reactor, the volume of steam and the amount of reflux are slightly larger than in Example 4-3 in which the primary alcohol is fed into the upper portion of the column, which is because the amount of heat fed to raise the temperature of the alcohol subjected to the rear-end feed to the temperature of the reactor was directly supplied from reactor steam. On the other hand, when the primary alcohol was fed to the upper portion of the column, gas/liquid separation of the column was performed, and thus, heat exchange was simultaneously performed, so that it can be confirmed that the amount of heat fed into the steam was reduced when compared to Examples 4-1 and 4-2. Examples 4-4 and 4-5 are cases in which there were two rear-end feed positions, wherein feed was commonly performed on the second reaction unit and the rear-end feed was performed on each of the third and fourth reaction units. Aside from the fact that the feed positions were different, the effect of reducing the volume of steam and the amount of reflux was evaluated as not being significantly different. However, since feed was performed on the last fourth reaction unit in Example 4-5, the temperature had to be raised to achieve a target conversion rate, and as a result, it was confirmed that the volume of steam supplied and the amount of reflux of the primary alcohol were increased compared to Example 4-4.

[Description of the Reference Numerals or Symbols]

| | |
|---|---|
| 10, 20, N0: Reaction unit | 14, 24, N4: Gas phase discharge line |
| 11, 21, N1: Reactor | 15, 25, N5: Liquid phase introduction line |
| 11a, 21a, N1a: Product line | |
| 11b, 21b, N1b: Raw material feed line | 16, 26, N6: Column upper line |
| 12, 22, N2: Column | 17, 27, N7: Organic layer line |
| 13, 23, N3: Layer separator | 18, 28, N8: Aqueous layer line |
| | 19, 29, N9: Condenser |

The invention claimed is:

1. A continuous production method of a diester-based material in a continuous production process comprising a reaction part in which a total of N reaction units from a first reaction unit to an N-th reaction unit are connected in series, the method comprising:
    feeding one or more dicarboxylic acids selected from the group consisting of terephthalic acid, phthalic acid, isophthalic acid, and cyclohexane dicarboxylic acid and a primary alcohol having 3 to 10 carbon atoms into the reaction part,
    wherein the feed of the primary alcohol is divided into a front-end feed of being fed into a first reaction unit and a rear-end feed of being fed into one or more reaction units selected among from a second reaction unit to an N-th reaction unit,
    wherein the amount of the rear-end feed is 5 to 80 wt % based on the total feed amount of the primary alcohol into the reaction part, and
    wherein N is an integer of 3 to 6.

2. The continuous production method of claim 1, wherein the amount of the rear-end feed is 10 to 70 wt % based on the total feed amount of the primary alcohol into the reaction part.

3. The continuous production method of claim 1, wherein the molar ratio of the feed amount of the one or more dicarboxylic acids to the total feed amount of the primary alcohol into the reaction part is 1:2 to 1:5.

4. The continuous production method of claim 1, wherein the molar ratio of the feed amount of the one or more dicarboxylic acids to the total feed amount of the primary alcohol into the reaction part is 1:2.5 to 1:4.

5. The continuous production method of claim 1, wherein the reaction unit comprises:
    a reactor in which an esterification reaction of dicarboxylic acid and a primary alcohol is performed;
    a column in which the primary alcohol vaporized during the esterification reaction and water are introduced from the reactor to cause gas-liquid separation and then a liquid phase is fed into a lower reactor and a gas phase is discharged from an upper portion of the column;
    a condenser which liquefies the gas phase discharged from the upper portion of the column and converts the liquefied gas phase into a liquid phase mixture; and
    a layer separator in which the layer separation of the liquid phase mixture into an organic layer and an aqueous layer is performed, and then the separated organic layer is fed into an upper end of the column.

6. The continuous production method of claim 1, wherein the rear-end feed is fed into the second reaction unit.

7. The continuous production method of claim 1, wherein the rear-end feed is fed into the second reaction unit and into any one reaction unit selected among from a third reaction unit to the N-th reaction unit.

8. The continuous production method of claim 1, wherein the production process further comprises a mixer at a front end of the reaction part, and the front-end feed of the primary alcohol is fed into the mixer or into the first reaction unit.

9. The continuous production method of claim 1, wherein N is an integer of 3 to 5.

10. The continuous production method of claim 1, wherein a feed position of the rear-end feed is selected from the group consisting of product line feed into a reactor feed line (A), reactor feed into a reactor (B), column upper portion feed (C), and column upper line feed (D).

* * * * *